United States Patent [19]

Kieslich

[11] 4,237,220

[45] Dec. 2, 1980

[54] PROCESS FOR PREPARING 9α-HYDROXY-4-ANDROSTENE-3,17-DIONE

[75] Inventor: Klaus Kieslich, Berlin, Fed. Rep. of Germany

[73] Assignee: Schering, Aktiengesellschaft, Berlin and Bergkamen, Fed. Rep. of Germany

[21] Appl. No.: 95,740

[22] Filed: Nov. 19, 1979

[30] Foreign Application Priority Data

Nov. 15, 1978 [DE] Fed. Rep. of Germany ....... 2850047

[51] Int. Cl.$^3$ .............................................. C12P 33/06
[52] U.S. Cl. ...................................... 435/58; 435/911

[58] Field of Search ..................................... 435/58, 61

[56] References Cited

U.S. PATENT DOCUMENTS

| | | | |
|---|---|---|---|
| 3,080,298 | 3/1963 | Principe et al. | 435/58 |
| 3,546,260 | 12/1970 | Pan et al. | 435/58 |

*Primary Examiner*—Alvin E. Tanenholtz
*Attorney, Agent, or Firm*—MIllen & White

[57] ABSTRACT

A high yield process for preparing 9α-hydroxy-4-androstene-3,17-dione comprises fermenting 4-androstene-3,17-dione with a culture of *Corynespora cassicola* ATCC 16,718.

1 Claim, No Drawings

PROCESS FOR PREPARING 9α-HYDROXY-4-ANDROSTENE-3,17-DIONE

BACKGROUND OF THE INVENTION

The present invention relates to a process for preparing 9α-hydroxy-4-androstene-3,17-dione.

9α-hydroxy-4-androstene-3,17-dione has been known for a long time (J. Am. Chem. Soc. 80, 1958, 6148) and has an outstanding antiandrogenous and antiestrogenous effect. It is also a valuable intermediate product for preparing 4,9(11)-androstadiene-3,17-dione which, in turn, can be converted by conventional methods into numerous pharmacologically active steroids.

When microbiologically preparing this compound from 4-androstene-3,17-dione by the previously conventional methods, only relatively low yields of the desired product are obtained. (See, e.g., Biotechnology and Bioengineering, XI, 1969, 1183; and U.S. Pat. Nos. 3,080,298 and 3,116,200.)

SUMMARY OF THE INVENTION

Accordingly, it is an object of this invention to provide a microbiological process for preparing 9α-hydroxy-4-androstene-3,17-dione in high yields.

Upon further study of the specification and appended claims, further objects and advantages of this invention will become apparent to those skilled in the art.

These objects have been achieved by providing a process for preparing 9α-hydroxy-4-androstene-3,17-dione comprising fermenting 4-androstene-3,17-dione with a culture of *Corynespora cassicola* ATCC 16,718.

DETAILED DISCUSSION

Using the process of this invention, it is possible to convert high substrate concentrations of 4-androstene-3,17-dione into 9α-hydroxy-4-androstene-3,17-dione at high yields, e.g., 80–100%, based on the amount of substrate starting material.

The process of this invention can be carried out under those conditions which ordinarily are appropriate for the microbiological hydroxylation of steroids. See, e.g., A. Capec et al. :Microbial Transformation of Steroids; Academic Press, Praque, 1966, page 65 to 68, whose disclosure is incorporated by reference herein.

Such conventional culture conditions include the use o submersion cultures bred in a suitable nutrient medium with aeration. The cultures are then added to the 4-androstene-3,17-dione (dissolved in a solvent or preferably in emulsified form) and fermentation takes place until a maximum conversion of the substrate is achieved.

Suitable substrate solvents for instance include methanol, ethanol, glycol-monomethylether, dimethylformamide and dimethylsulfoxide. The substrate for instance may be emulsified by nozzle-injecting it in micronized form or dissolved in a water miscible solvent (such as methanol, ethanol, acetone, glycol-monomethylether, dimethylformamide or dimethylsulfoxide) in the presence of strong turbulence in (preferably decalcified) water containing the conventional emulsifying adjuvants. Suitable emulsifying adjuvants include non-ionic emulsifiers, for instance, ethyleneoxy adducts or fatty acid esters of polyglycols. Suitable emulsifiers include the conventional commercial wetting agents Tegin ®, Tween ® and Span ®.

Process details such as the optimal substrate concentration, the substrate addition time(s), and the duration of fermentation depend on the conditions of fermentation which are used. As is the general conventional procedure for microbiological steroid conversions, these values must be ascertained in each case by routine preliminary tests which are fully conventional for one of ordinary skill in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

500 ml of a sterilized medium in a 2-liter Erlenmeyr flask and containing 6% liquid dextrin (corresponding to 3% solid glucose), with 1% Corstep liquor
0.2% sodium nitrate
0.1% potassium dihydrogen phosphate
0.2% dipotassium hydrogen phosphate
0.05% magnesium sulfate
0.002% iron (II) sulfate
0.05% potassium chloride is inoculated with an elutriation of an oblique agar culture of *Corynespora cassicola* ATCC 16,718 which is from one to two weeks old. After a three-day growth on a rotation shaker at 30° C., the mycelium suspension is used to inoculate a 30-liter test fermenter loaded with 25 liters of a sterilized medium of the same composition. Germination is carried out at 29° C. with aeration of 25 l/min and a stirring rate of 220 rpm and with occasional addition of Polyol 2000 as an antifoaming agent. After 48 hours, 1.5 liters of the culture is transferred under sterile conditions into a fermenter of the same size which is loaded with 23.5 liters of a sterile nutrient solution of the same composition. After 6 hours, a sterile filtered solution of 12.5 g of 4-androstene-3,17-dione in 100 ml of dimethylformamide is added. This substrate addition is repeated after 15 and 20 hours so that a substrate concentration of 1.5 g/l is obtained. The conversion is monitored by removing several samples extracted by methylisobutylketone and analyzing them by thin film chromatography using Merck silica plates 60 F-254 (development: chloroform/methane, 9+1). After a total of about 38 hours of total fermentation time, the initial material is entirely converted.

The fermenting equipment is harvested by centrifuging the mycelium and by extracting three times with methylisobutylketone. The mycelium also is rinsed three times with methylisobutylketone. The combined extracts and rinse solutions are concentrated in vacuum, the amount of pure product crystallizing during the concentration being filtered off. 13.1 g are so obtained (melting point 217/219°–221° C.).

The extract concentrate is concentrated until dry; the residue is rinsed free from the antifoam agent by means of hexane and is recrystallized from acetic ester. An additional 14.4 g are obtained as first and second crystallizates (melting point 217/218°–220° C.). As shown by spectral data, the product consists uniformly of 9α-hydroxy-4-androstene-3,17-dione. The total yield is 69.5% of the theoretical.

EXAMPLE 2

Under the same conditions used in Example 1, 13 liters of a well-developed culture of *Corynespora cassicola* ATCC 16,718 is prepared and loaded with 500 ml of substrate suspension at each of the times: 15, 20, 25 and 30 hours. This substrate suspension is prepared each time for two hours by grinding 37.5 g of the substrate in 500 ml of 2% Tween® 80 solution in a ball mill. The substrate suspension is pasteurized at 100° C.

After 92 hours of total fermentation, the substrate is converted. It is harvested and reprocessed as described in Example 1. Upon concentrating the methylisobutylketone extracts, 30 g of raw product is obtained. These are recrystallized from acetic ester and yield 25 g of pure product. The 50 g of raw product obtained by rinsing the mycelium provides an additional 41 g of pure product recrystallized from acetic ester. The melting point is 218/219°–221° C. and the total yield is 70% of the theoretical. Additional amounts of product can be obtained by purifying the mother liquors chromatographically.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing 9α-hydroxy-4-androstene-3,17-dione, comprising, fermenting 4-androstene-3,17-dione with a culture of *Corynespora cassicola* ATCC 16,718.

* * * * *